US011203625B2

(12) United States Patent
Lisonbee et al.

(10) Patent No.: US 11,203,625 B2
(45) Date of Patent: *Dec. 21, 2021

(54) COMPOSITIONS INCLUDING DIFFERENT TYPES OF TRANSFER FACTOR

(71) Applicant: 4Life Patents, LLC, Sandy, UT (US)

(72) Inventors: David Lisonbee, Orem, UT (US); William J. Hennen, Eagle Mountain, UT (US); F. Joseph Daugherty, Omaha, NE (US)

(73) Assignee: 4LIFE PATENTS, LLC, Sandy, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 16/673,651

(22) Filed: Nov. 4, 2019

(65) Prior Publication Data

US 2020/0062815 A1 Feb. 27, 2020

Related U.S. Application Data

(63) Continuation of application No. 11/377,703, filed on Mar. 15, 2006, now Pat. No. 10,464,980, which is a continuation-in-part of application No. PCT/US2004/030307, filed on Sep. 15, 2004, which is a continuation of application No. 10/663,353, filed on Sep. 15, 2003, now Pat. No. 6,866,868.

(51) Int. Cl.
| | |
|---|---|
| *A61K 35/20* | (2006.01) |
| *A61K 35/57* | (2015.01) |
| *C07K 14/52* | (2006.01) |
| *A61J 3/07* | (2006.01) |
| *C07K 14/465* | (2006.01) |
| *A61K 35/00* | (2006.01) |

(52) U.S. Cl.
CPC .............. *C07K 14/52* (2013.01); *A61J 3/074* (2013.01); *A61K 35/20* (2013.01); *A61K 35/57* (2013.01); *C07K 14/465* (2013.01); *A61K 35/00* (2013.01)

(58) Field of Classification Search
None
See application file for complete search history.

(56) References Cited

U.S. PATENT DOCUMENTS

| | | | |
|---|---|---|---|
| 4,180,627 A | 12/1979 | Klesius et al. | |
| 4,402,938 A | 9/1983 | Collins et al. | |
| 4,816,563 A | 3/1989 | Wilson et al. | |
| 5,001,225 A | 3/1991 | Taylor | |
| 5,080,895 A | 1/1992 | Tokoro | |
| 5,367,054 A | 11/1994 | Lee | |
| 5,470,835 A | 11/1995 | Kirkpatrick et al. | |
| 5,538,727 A | 7/1996 | Stolle et al. | |
| 5,753,228 A | 5/1998 | Sterling et al. | |
| 5,753,268 A | 5/1998 | Stolle et al. | |
| 5,840,700 A | 11/1998 | Kirkpatrick et al. | |
| 5,849,349 A | 12/1998 | Stolle et al. | |
| 5,853,765 A | 12/1998 | Stolle et al. | |
| 6,468,534 B1 | 10/2002 | Hennen et al. | |
| 6,866,868 B1* | 3/2005 | Lisonbee | A61K 35/20 424/535 |
| 10,464,980 B2* | 11/2019 | Lisonbee | C07K 14/52 |
| 10,471,100 B2* | 11/2019 | Lisonbee | A61P 37/02 |
| 2002/0044942 A1 | 4/2002 | Dopson | |
| 2004/0126432 A1 | 7/2004 | Hennen | |
| 2005/0233967 A1 | 10/2005 | Dadali et al. | |

FOREIGN PATENT DOCUMENTS

| | | | |
|---|---|---|---|
| AU | 2004274928 B2 | 6/2010 | |
| AU | 2010221798 B2 | 1/2013 | |
| CN | 1901925 A | 1/2007 | |
| CN | 100546650 C | 10/2009 | |
| CN | 101669969 A | 3/2010 | |
| EP | 0143445 A2 | 6/1985 | |
| EP | 0914831 * | 5/1999 | ............. A61K 39/42 |
| EP | 0930316 A1 | 7/1999 | |
| EP | 1670894 A2 | 6/2006 | |
| JP | 4880463 B2 | 2/2012 | |
| MX | 273010 | 12/2009 | |
| MX | 287426 | 6/2011 | |

(Continued)

OTHER PUBLICATIONS

USPTO as International Searching Authority, "International Search Report and Written Opinion," International Application No. PCT/US2004/030307, dated Jul. 7, 2006.
European Patent Office, "Supplementary European Search Report", European Application No. 04784242.2, dated May 12, 2009.
Memorial Sloan-Kettering Center, "Transfer Factor," accessed on the internet at <http://www.mskcc.org/print/cancer-care/herb/transfer-factor> (Aug. 9, 2012).
Jun, HS, et al., "A new look at viruses in type I diabetes," Diabetes Metab Res Rev 1:8-31 (2003).
Flodstrom, M, et al., "Diabetogenic potential of human pathogens uncovered in experimentally permissive beta-cells," Diabetes 52:2025-2034 (2003).
Zhou et al., "Specificity and degeneracy: T cell recognition in CNS autoimmunity," Mol Immunol 40:1057-61 (2004).

(Continued)

*Primary Examiner* — Allison M Fox
(74) *Attorney, Agent, or Firm* — Dentons Durham Jones Pinegar

(57) ABSTRACT

A composition for eliciting a T-cell mediated immune response in a subject includes transfer factor from at least two different types of source animals. For example, the composition may include mammalian transfer factor and nonmammalian transfer factor. An example of the composition includes a combination of a colostrum-derived product, which includes the mammalian transfer factor, and an egg-derived product, which includes the nonmammalian transfer factor. Additionally, the egg-derived product may be substantially free of fat. Methods for forming the composition and eliciting T-cell mediated immune responses in subjects that have been treated with the composition are also disclosed.

18 Claims, 2 Drawing Sheets

(56) References Cited

FOREIGN PATENT DOCUMENTS

WO    2002/024746 A1    3/2002

OTHER PUBLICATIONS

Horwitz, MS, et al., "Coxsackieviral-mediated diabetes: induction requires antigen-presenting cells and is accompanied by phagocytosis of beta cells"; Clin Immunol 110:134-144 (2004).
Navratil, JS, et al., "Apoptosis and immune responses to self," Rheum Dis Clin North Am 30:193-212 (2004).
Christen, U, et al., "Virally induced inflammation triggers fratricide of Fas-ligand-expressing beta cells," Diabetes 53:591-596 (2004).
Newswanger, DL, et al., "Guillain-Barre Syndrome," Am Fam Physician 69:2405-2410 (2004).
Fabio, "Immune Milk," The Arthritis Trust, Spring 2000, pp. 1-8.
Kliesius, PH, et al., "Adoptive Transfer of Delayed Hypersensitivity and Protective Immunity to Eimeria tenella with Chicken-Derived Transfer Factor," Poult Sci 63:1333-1337 (1984).
Giambrone, JJ, et al., "Adoptive Transfer of Delayed Wattle Reactivity in Chickens with a Dialyzable Leukocyte Extract Containing Transfer Factor," Poult Sci 62:767-771 (1983).
Fudenberg, HH, et al., "Transfer Factor 1993: New Frontiers," Prog Drug Res 42:309-318 (1994).
Qureshi, MA, et al., "Understanding Immunology in Disease Development and Control," Poult Sci 77:1126-1129 (1998).
Sharma, JM, "The Structure and Function of the Avian Immune System," Acta Veterinaria Hungarica, 45(3):229-238 (1997).
XIth International Congress on Transfer Factor, Universidad Autonoma de Nuevo Leon, Mar. 1999.
Egcel™ and BioChoice™, Overview for Health Care Professionals, DCV, Apr. 1999, pp. 1-4.
Millipore Sterile Membrane Filters, httll://www.millillQre.com.
Celite Filter Media; RH 1010, Funnel, Buchner Type; http://www.celtic-eng.ie/celite/htm; http://www.glassfilter/.com and http://www.worldminerals.com.
Dekich, MA "Broiler Industry Strategies for Control of Respiratory and Enteric Diseases," Poult Sci 77:1176-1180 (1998).
Akari, H, et al., "Prophylaxis of experimental HTLV-1 infection in cynomolgus monkeys by passive immunization," Vaccine 15:1391-1395(1997).
Bende, S, et al., "HIV prevention research: progress and challenges in the new millennium," AIDScience, 1(3) (Jun. 2001).
Barouch, DH, et al., "Eventual AIDS vaccine failure in a rhesus monkey by viral escape from cytotoxic T lymphocytes," Nature 415:335-339 (2002).

\* cited by examiner

COMPOSITIONS INCLUDING DIFFERENT TYPES OF TRANSFER FACTOR

CROSS-REFERENCE TO RELATED APPLICATIONS

This application is a continuation of U.S. patent application Ser. No. 11/377,703, filed Mar. 15, 2006, titled COMPOSITIONS INCLUDING DIFFERENT TYPES OF TRANSFER FACTOR, now U.S. Pat. No. 10,464,980, issued Nov. 5, 2019 ("the '703 Application"), which is a continuation-in-part of PCT international patent application no. PCT/US2004/030307, filed Sep. 15, 2004 ("the '307 International Application"), which claims the benefit of the filing date of U.S. patent application Ser. No. 10/663,353, filed Sep. 15, 2003, now U.S. Pat. No. 6,866,868, issued Mar. 15, 2005 ("the '353 Application"). The entire disclosures of each of the '703 Application, the '307 International Application, and the '353 Application are hereby incorporated herein.

TECHNICAL FIELD

The present invention relates generally to compositions which include transfer factor and, more specifically, to compositions which include transfer factor from different types of source animals. The present invention also relates to methods for making compositions that include different types of transfer factor and to methods for eliciting or enhancing a T-cell mediated immune response by the immune system of a subject.

RELATED ART

Many deadly pathogens are passed to humans from the animal kingdom. For example, monkeys are the sources of the type I human immunodeficiency virus (HIV-I), which causes acquired immune deficiency syndrome (AIDS) and monkeypox, which is similar to smallpox; ground-dwelling mammals are believed to be the source of the Ebola virus; fruit bats and pigs are the source of the Nipah virus; the Hendra virus comes from horses; the virus responsible for the "Hong Kong Flu" originated in chickens; and wild birds, especially ducks, are the sources of many of the deadly influenza viruses. Many diseases also have animal reservoirs. By way of example, mice carry Hanta virus, rats carry the Black Plague, and deer carry Lyme disease.

The Immune System

The immune systems of vertebrates are equipped to recognize and defend the body from invading pathogenic organisms, such as parasites, bacteria, fungi, and viruses. Vertebrate immune systems typically include a cellular component and a noncellular component.

The cellular component of an immune system includes the so-called "lymphocytes," or white blood cells, of which there are several types. It is the cellular component of a mature immune system that typically mounts a primary, nonspecific response to invading pathogens, as well as being involved in a secondary, specific response to pathogens.

In the primary, or initial, response to an infection by a pathogen, white blood cells that are known as phagocytes locate and attack the invading pathogens. Typically, a phagocyte will internalize, or "eat" a pathogen, then digest the pathogen. In addition, white blood cells produce and excrete chemicals in response to pathogenic infections that are intended to attack the pathogens or assist in directing the attack on pathogens.

Only if an infection by invading pathogens continues to elude the primary immune response is a specific, secondary immune response to the pathogen needed. As this secondary immune response is typically delayed, it is also known as "delayed-type hypersensitivity." A mammal, on its own, will typically not elicit a secondary immune response to a pathogen until about seven (7) to about fourteen (14) days after becoming infected with the pathogen. The secondary immune response is also referred to as an acquired immunity to specific pathogens. Pathogens have one or more characteristic proteins, which are referred to as "antigens." In a secondary immune response, white blood cells known as B lymphocytes, or "B-cells," and T lymphocytes, or "T-cells," "learn" to recognize one or more of the antigens of a pathogen. The B-cells and T-cells work together to generate proteins called "antibodies," which are specific for (e.g., configured to bind to or otherwise "recognize") one or more certain antigens on a pathogen.

The T-cells are primarily responsible for the secondary, or delayed-type hypersensitivity, immune response to a pathogen or antigenic agent. There are three types of T-cells: T-helper cells, T-suppressor cells, and antigen-specific T-cells, which are also referred to as cytotoxic (meaning "cell-killing") T-lymphocytes (CTLs), or T-killer cells or natural killer (NK) cells. The T-helper and T-suppressor cells, while not specific for certain antigens, perform conditioning functions (e.g., the inflammation that typically accompanies an infection) that assist in the removal of pathogens or antigenic agents from an infected host. The NK cells, which comprise about ten to about fifteen percent of circulating lymphocytes, are important mediators of both natural and adaptive immunity.

Antibodies, which make up only a part of the noncellular component of an immune system, recognize specific antigens and, thus, are said to be "antigen-specific." The generated antibodies then basically assist the white blood cells in locating and eliminating the pathogen from the body. Typically, once a white blood cell has generated an antibody against a pathogen, the white blood cell and all of its progenitors continue to produce the antibody. After an infection is eliminated, a small number of T-cells and B-cells that correspond to the recognized antigens are retained in a "resting" state. When the corresponding pathogenic or antigenic agents again infect the host, the "resting" T-cells and B-cells activate and, within about forty-eight (48) hours, induce a rapid immune response. By responding in this manner, the immune system mounts a secondary immune response to a pathogen, the immune system is said to have a "memory" for that pathogen.

Mammalian immune systems are also known to produce smaller proteins, known as "transfer factors," as part of a secondary immune response to infecting pathogens. Transfer factors are another noncellular part of a mammalian immune system.

Antigen-specific transfer factors are believed to be structurally analogous to antibodies, but on a much smaller molecular scale. Both antigen-specific transfer factors and antibodies include antigen-specific sites. In addition, both transfer factors and antibodies include highly conserved regions that interact with receptor sites on their respective effector cells. In transfer factor and antibody molecules, a third, "linker," region connects the antigen-specific sites and the highly conserved regions.

The Role of Transfer Factor in the Immune System

Transfer factor is a low molecular weight isolate of lymphocytes. Narrowly, transfer factors may have specificity for single antigens. U.S. Pat. Nos. 5,840,700 and 5,470,835, both of which issued to Kirkpatrick et al. (hereinafter collectively referred to as "the Kirkpatrick Patents"), disclose the isolation of transfer factors that are specific for certain antigens. More broadly, "specific" transfer factors have been generated from cell cultures of monoclonal lymphocytes. Even if these transfer factors are generated against a single pathogen, they have specificity for a variety of antigenic sites of that pathogen. Thus, these transfer factors are said to be "pathogen-specific" rather than antigen-specific. Similarly, transfer factors that are obtained from a host that has been infected with a certain pathogen are pathogen-specific. Although such preparations are often referred to in the art as being "antigen-specific" due to their ability to elicit a secondary immune response when a particular antigen is present, transfer factors having different specificities may also be present in such preparations. Thus, even the so-called "antigen-specific," pathogen-specific transfer factor preparations may be specific for a variety of antigens.

Additionally, it is believed that antigen-specific and pathogen-specific transfer factors may cause a host to elicit a delayed-type hypersensitivity immune response to pathogens or antigens for which such transfer factor molecules are not specific. Transfer factor "draws" at least the non-specific T-cells, the T-inducer and T-suppressor cells, to an infecting pathogen or antigenic agent to facilitate a secondary, or delayed-type hypersensitivity, immune response to the infecting pathogen or antigenic agent.

Typically, transfer factor includes an isolate of proteins having molecular weights of less than about 10,000 daltons (D) that have been obtained from immunologically active mammalian sources. It is known that transfer factor, when added either in vitro or in vivo to mammalian immune cell systems, improves or normalizes the response of the recipient mammalian immune system.

The immune systems of newborns have typically not developed, or "matured," enough to effectively defend the newborn from invading pathogens. Moreover, prior to birth, many mammals are protected from a wide range of pathogens by their mothers. Thus, many newborn mammals cannot immediately elicit a secondary response to a variety of pathogens. Rather, newborn mammals are typically given secondary immunity to pathogens by their mothers. One way in which mothers are known to boost the immune systems of newborns is by providing the newborn with a set of transfer factors. In mammals, transfer factor is provided by a mother to a newborn in colostrum, which is typically replaced by the mother's milk after a day or two. Transfer factor basically transfers the mother's acquired, specific (i.e., delayed-type hypersensitive) immunity to the newborn. This transferred immunity typically conditions the cells of the newborn's immune system to react against pathogens in an antigen-specific manner, as well as in an antigen- or pathogen-nonspecific fashion, until the newborn's immune system is able on its own to defend the newborn from pathogens. Thus, when transfer factor is present, the immune system of the newborn is conditioned to react to pathogens with a hypersensitive response, such as that which occurs with a typical delayed-type hypersensitivity response. Accordingly, transfer factor is said to "jump start" the responsiveness of immune systems to pathogens.

Much of the research involving transfer factor has been conducted in recent years. Currently, it is believed that transfer factor is a protein with a length of about forty-four (44) amino acids. Transfer factor typically has a molecular weight in the range of about 3,000 to about 5,000 Daltons (Da), or about 3 kDa to about 5 kDa, but it may be possible for transfer factor molecules to have molecular weights outside of this range. Transfer factor is also believed to include three functional fractions, each of which may include different types of transfer factor molecules: an inducer fraction; an immune suppressor fraction; and an antigen-specific fraction. Many in the art believe that transfer factor also includes a nucleoside portion, which could be connected to the protein molecule or separate therefrom, that may enhance the ability of transfer factor to cause a mammalian immune system to elicit a secondary immune response. The nucleoside portion may be part of the inducer or suppressor fractions of transfer factor.

The antigen-specific region of the antigen-specific transfer factors is believed to comprise about eight (8) to about twelve (12) amino acids. A second highly-conserved region of about ten (10) amino acids is thought to be a very high-affinity T-cell receptor binding region. The remaining amino acids may serve to link the two active regions or may have additional, as yet undiscovered properties. The antigen-specific region of a transfer factor molecule, which is analogous to the known antigen-specific structure of an antibody, but on a much smaller molecular weight scale, appears to be hyper-variable and is adapted to recognize a characteristic protein on one or more pathogens. The inducer and immune suppressor fractions are believed to impart transfer factor with its ability to condition the various cells of the immune system so that the cells are more fully responsive to the pathogenic stimuli in their environment.

Sources of Noncellular Immune System Components

Conventionally, transfer factor has been obtained from the colostrum of milk cows, such as by the method described in U.S. Pat. No. 4,816,563 to Wilson et al. (hereinafter "Wilson"). While milk cows typically produce large amounts of colostrum and, thus, large amounts of transfer factor over a relatively short period of time, milk cows only produce colostrum for about a day or a day-and-a-half every year. Thus, milk cows are neither a constant source of transfer factor nor an efficient source of transfer factor.

Transfer factor has also been obtained from a wide variety of other mammalian sources. For example, in researching transfer factor, mice have been used as a source for transfer factor. Antigens are typically introduced subcutaneously into mice, which are then sacrificed following a delayed-type hypersensitivity reaction to the antigens. Transfer factor is then obtained from spleen cells of the mice.

While different mechanisms are typically used to generate the production of antibodies, the original source for antibodies may also be mammalian. For example, monoclonal antibodies may be obtained by injecting a mouse, a rabbit, or another mammal with an antigen, obtaining antibody-producing cells from the mammal, then fusing the antibody-producing cells with immortalized cells to produce a hybridoma cell line, which will continue to produce the monoclonal antibodies throughout several generations of cells and, thus, for long periods of time.

Antibodies against mammalian pathogens have been obtained from a wide variety of sources, including mice, rabbits, pigs, cows, and other mammals. In addition, the pathogens that cause some human diseases, such as the common cold, are known to originate in birds. As it has become recognized that avian (i.e., bird) immune systems and mammalian immune systems are very similar, some researchers have turned to birds as a source for generating antibodies.

Avian antibodies that are specific for pathogens that infect mammals, or "mammalian pathogens," have been obtained by introducing antigens into eggs. Alternatively, antibodies may be present in eggs following exposure of the source animal to antigens, including antigens of mammalian pathogens. U.S. Pat. No. 5,080,895, issued to Tokoro on Jan. 14, 1992 (hereinafter "the '895 Patent"), discloses a method that includes injecting hens with pathogens that cause intestinal infectious diseases in neonatal mammals. The hens then produce antibodies that are specific for these pathogens, which are present in eggs laid by the hens. The '895 Patent discloses compositions that include these pathogen-specific antibodies and use thereof to treat and prevent intestinal diseases in neonatal piglets and calves. Treatment of pathogenic infections in mammals with avian antibodies may have undesirable results, however, since the immune systems of mammals may respond negatively to the large avian antibody molecules by eliciting an immune response to the antibodies themselves. Moreover, as mammalian immune systems do not recognize avian antibodies as useful for their abilities to recognize certain pathogens, or the specificities of avian antibodies for antigens of such pathogens, avian antibodies often do not elicit the desired immune responses in mammals.

It is also known that transfer factor may be obtained from eggs. U.S. Pat. No. 6,468,534 to Hennen et al. (hereinafter "Hennen") describes a process by which female chickens (i.e., hens) are exposed to one or more antigens, which results in the elicitation of an immune response, including a secondary immune response, by the chickens. As a result of the secondary immune response, transfer factor molecules are present in the eggs of the chicken. The eggs may then be processed to provide a product in which the transfer factor is present. Such a product may take the form of a spray dried or freeze dried, or lyophilized, egg powder, and may include all or part of the egg. The egg powder may then be incorporated directly into gelatin capsules or mixed with other substances then introduced into gelatin capsules.

FIG. 2 schematically depicts capsulation equipment of a type that is currently useful for capsulating egg-derived avian transfer factor in the form of an egg powder. Capsulation equipment 20 includes a composition supply hopper 24, a feed station 28, and an auger 26 in communication between each composition supply hopper 24 and feed station 28. Auger 26 transports the whole egg powder from composition supply hopper 24 to feed station 28.

When auger 26 operates, it is heated to a temperature that exceeds the relatively low melting point of cholesterol, from egg yolk, in the egg powder. The warmed cholesterol is sticky, coating auger 26, the conduit in communication therewith, and feed station 28, thereby decreasing the efficiency with which capsulation equipment 20 operates. Consequently, capsulation equipment 20 must be disassembled and cleaned periodically, which may take a considerable amount of time (e.g., up to about 8 hours), resulting in a significant decrease in the productivity of capsulation equipment 20 and, thus, the number of capsules that may be formed therewith. Thus, processing of whole egg powder to obtain a transfer factor-containing product is somewhat undesirable.

Additionally, compositions which are derived from products (e.g., eggs or colostrum) from a single source animal typically only include transfer factor molecules which have specificity to antigens to which the source animal has been exposed. The consequence of such limited exposure may be that the effectiveness of such transfer factor-containing compositions in preventing or treating certain types of infections or conditions is also limited.

Accordingly, there is a need for a composition which is useful for causing an immune system of a treated subject to elicit an immune response to a broader array of pathogens, as well as for a method for improving the efficiency and productivity with which capsulation and other composition-forming equipment operates.

SUMMARY OF THE INVENTION

The present invention includes compositions for eliciting T-cell mediated immune responses in subjects. The composition includes an active component with transfer factor from at least two different types of source animals. The term "type," as used herein with respect to source animals, describes the source animals from which transfer factor may be obtained and refers to source animals from different classes (e.g., mammals, birds, reptiles, amphibians, insects, etc.). The term "type," as used herein, also refers to source animals from different subclasses, orders (e.g., artiodactyls, primates, carnivores, etc.), families (bovine, hominids, felines, etc.), subfamilies, genuses (e.g., cattle, humans, domestic cats, etc.), and even species and subspecies. Use of the term "type" herein with respect to transfer factor denotes the type of source animal from which the transfer factor was obtained.

An exemplary embodiment of the active component of such a composition includes transfer factor from both mammalian and nonmammalian source animals, which types of transfer factor are also referred to herein as "mammalian transfer factor" and "nonmammalian transfer factor," respectively. By way of nonlimiting example, the mammalian transfer factor may be included in the composition as colostrum or a fraction or extract thereof, which are collectively referred to herein as "colostrum-derived products," or otherwise, as known in the art (e.g., as a cellular extract, such as a leukocyte (white blood cell) extract, a splenic ("from the spleen") extract, or the like, etc.). Also by way of example, the nonmammalian transfer factor of the exemplary composition may be obtained from an egg or a fraction or extract thereof, which are also referred to herein as "egg-derived products." It has been discovered that when different types of transfer factors are combined and administered to a treated animal (e.g., a mammal), some synergy occurs.

When a composition of the present invention includes a colostrum-derived product and an egg-derived product, both products may be included in the mixture in amounts (e.g., by weight, by volume, etc., of the total mixture) that are about equal, or more of one of the colostrum-derived product and the egg-derived product than the other. Experimental results show that transfer factor from source animals that have highly dependent young, such as cows, induces a relatively quick secondary immune response, with anergy (i.e., a lack of sensitivity by white blood cells to the transfer factor molecules) setting in relatively quickly.

The different types of transfer factor of the active component may be selected or provided in amounts that are tailored to cause a treated subject to synergistically elicit a T-cell mediated immune response. For example, transfer factor from source animals that have independent young, such as chickens or other "gallinaceous" birds, does not induce as quick a secondary immune response, but does provide for a more sustained secondary immune response. Accordingly, the relative concentrations of colostrum-derived transfer product and egg-derived product may be tailored to elicit a secondary immune response that occurs or is sustained for a particular period of time. As another example of such synergism, transfer factor from one source may facilitate elicitation of a cell-mediated immune response against a corresponding set of pathogens or other antigenic agents, while transfer factor from another source may cause a treated subject to elicit a cell-mediated response against another set of pathogens or other antigenic agents. As a further example, one set of pathogens against which transfer factor from one source (e.g., from a source animal that has been exposed to a broad array of pathogens or other antigenic agents) is most effective may cause a subject to elicit a broad, or unfocused immune response, while transfer factor from another source (e.g., a source from a source animal that has been exposed to a limited number (e.g., only one or a few) pathogens or other antigenic agents) may cause a subject to elicit a narrow, focused immune response.

An active component of such a composition may consist essentially of the two or more types of transfer factor (including dialysate or another at least partially purified fraction having an upper-end molecular weight cutoff of about 10,000 Da), or include additional components.

Additional components may include a variety of different things, such as a portion of a source (e.g., egg, colostrum, cells, etc.) from which the transfer factor was derived, a supplement, beneficial microorganisms, and the like.

If a portion, or extract, of a source of transfer factor is included in a composition according to the present invention, the extract may be purified at least partially to remove one or more components therefrom. By way of nonlimiting example, proteins (e.g., antibodies and other proteins having molecular weights of about 160,000 Da or more), fat, casein, cells, or cell debris may be substantially removed from the extract and, thus, the extract, or even the composition, may be substantially free of these components. Allergenic components, including, but not limited to, some of the components listing immediately above, may also be separated from the transfer factor from at least one source. Of course, there is no requirement that any components be substantially removed from non-transfer factor portions of one or more sources, or that the non-transfer factor portions of one or more sources otherwise be purified.

Supplements are also referred to herein as "supplemental components." A supplement that may be included in a composition of the present invention includes, without limitation, one or more vitamins, minerals, proteins, or natural products (e.g., herbs, mushrooms, roots, etc.) or extracts thereof. Polysaccharides are believed to provide further synergy in the effectiveness of a composition of the present invention in eliciting secondary immune responses in treated animals. Exemplary polysaccharides are available in the form of beta-glucans and mushroom extracts (which, of course, include other components).

While a composition according to the present invention may also or alternatively include one or more beneficial microorganisms, compositions that incorporate teachings of the present invention may also lack microorganisms and, thus, be microorganism-free or cell-free.

According to another aspect, the present invention includes methods for forming compositions that include two or more types of transfer factor. One or more of transfer factor (e.g., colostrum, eggs, cells, tissues, etc.) may be processed to obtain and, optionally, at least partially purify transfer factor. Such processing may also be used to obtain, extract, or at least partially purify other components from the one or more sources. For example, processes such as those disclosed in Wilson and Hennen, may be employed. If desired, other components may be included in the composition.

In another aspect, the present invention includes a method for processing or manufacturing an egg-derived product which includes transfer factor. The inventive method of processing or manufacture includes mixing a substantially fat-free component, such as a colostrum-derived product, which may or may not include transfer factor, with the egg-derived product before or while the egg-derived product is being introduced into manufacturing or other processing equipment. Capsulation is one example of a processing or manufacturing method in which such techniques may be employed.

Additionally, the present invention includes a method for reducing the cleaning frequency of manufacturing or other processing equipment, such as capsulation equipment, used for processing an egg-derived product. That method includes mixing a less fatty or substantially fat free substance, such as a colostrum-derived product, with the egg-derived product before or during introduction of the egg-derived product into the processing equipment.

The present invention also includes methods for treating a subject. Treatment methods that incorporate teachings of the present invention include administration of a composition according to the present invention to a subject. As the composition includes transfer factor, administration of the composition to the subject will cause the subject's immune system to elicit a T-cell mediated immune response or will enhance a T-cell mediated immune response by the subject's immune system which is already underway.

Other features and advantages of the present invention will become apparent to those of ordinary skill in the art through consideration of the ensuing description, the accompanying drawings, and the appended claims.

BRIEF DESCRIPTION OF THE DRAWINGS

In the drawings, which depict exemplary embodiments of various aspects of the present invention.

DETAILED DESCRIPTION

Figure 1:
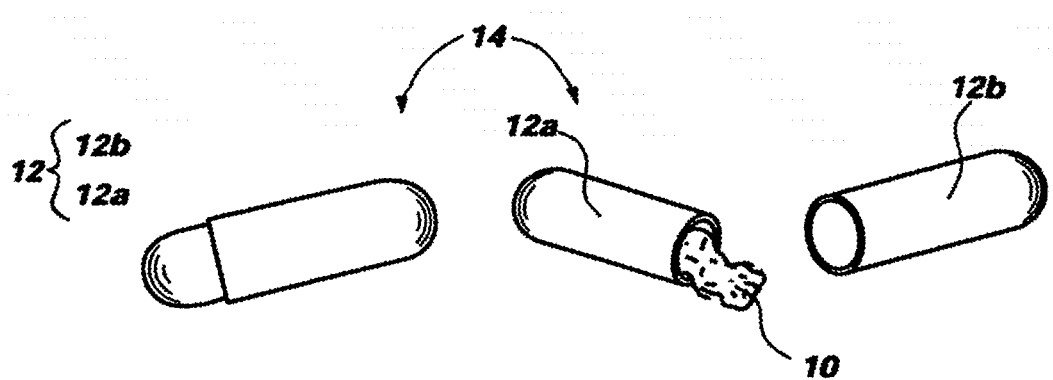
FIG. 1 depicts an example of the manner in which a composition that incorporates teachings of the present invention may be embodied.

An exemplary embodiment of composition that incorporates teachings of the present invention includes transfer factor from at least two different types of source animals. By way of nonlimiting example, a composition according to the present invention may include mammalian transfer factor and nonmammalian transfer factor.

The different types of transfer factor of the inventive composition may be obtained from any suitable source. For example, mammalian transfer factor may be obtained from colostrum, as described in Wilson or otherwise as known in the art (e.g., a leukocyte (white blood cell) extract, a splenic (i.e., "from the spleen") extract, etc.). An exemplary source for nonmammalian transfer factor is an egg of an animal, such as a chicken, as described in Hennen. Thus, a composition according to the present invention may include a first component which comprises colostrum or a fraction or extract thereof, which are collectively referred to herein as a "colostrum-derived product," as well as a second component that comprises egg or a fraction or extract thereof, which are also referred to herein as an "egg-derived products."

As compositions that incorporate teachings of the present invention include transfer factor from different types of source animals, they may include transfer molecules with a broader array of antigen-specificity or pathogen-specificity than conventional transfer factor-containing compositions. Thus, a composition according to the present invention is capable of enlisting the immune system of a treated animal to elicit a T-cell mediated immune response against a broader array of pathogens than those against which conventional transfer factor-containing compositions are effective. This is because different types of animals may be exposed to different types of antigens or pathogens, such as by vaccination, the animals' environments, or the like. Moreover, it is known that some conditions in certain animals are caused by multiple infections, even further expanding the specificity of a composition according to the present invention. For example, one or more pathogens may adversely affect (e.g., suppress or monopolize) the host's immune system, while one or more other pathogens may be permitted to cause a disease state in the host. As another example, some disease states are caused by a combination of pathogens.

As an example, a composition which includes transfer factor-containing components from both cows and chickens will include transfer factor molecules which are specific to antigens or pathogens to which cows are exposed, as well as transfer factor molecules that have specificity for antigens or pathogens to which chickens are exposed. As both cows and chickens may be exposed to antigens or pathogens to which the other is not exposed, such a composition may include transfer factor molecules with antigen or pathogen specificities that would not be present in a composition that includes only transfer factor from cows (e.g., by way of a colostrum-derived product) or transfer factor from chickens (e.g., through an egg-derived product).

A composition of the present invention may include about the same amounts, measured in terms of weight or volume, of a colostrum-derived product and an egg-derived product (i.e., about 50% colostrum-derived product and about 50% egg-derived product). Alternatively, a composition that incorporates teachings of the present invention may include more colostrum-derived product (e.g., about 85% or 60%, by combined weight of the colostrum-derived product and egg-derived product) than egg-derived product (about 15% or 40%, by weight). As another alternative, the inventive composition may include more egg-derived product (e.g., about 60% or 85%, by weight) than colostrum-derived product (e.g., about 40% or 15% by weight). As another example, a composition that incorporates teachings of the present invention may include about one percent, by weight, of one of a colostrum-derived product and an egg-derived product and about 99%, by weight, of the other of the colostrum-derived product and the egg-derived product. Although specific amounts of colostrum-derived product and egg-derived product have been provided, any combination thereof is within the scope of the present invention.

In addition to including a source of transfer factor (e.g., a colostrum-derived product, an egg-derived product, etc.) a composition that incorporates teachings of the present invention may include one or more other ingredients, including, but not limited to, vitamins, minerals, proteins, natural products (e.g., herbs, mushrooms, roots, etc., or extracts thereof), and the like. Additional ingredients may be useful for providing further advantages to subjects to which the composition is administered, or may enhance the ability of the transfer factor in the composition to elicit or enhance a secondary, or delayed-type hypersensitivity, immune response.

As shown in FIG. 1, without limiting the scope of the present invention, a composition 10 according to the present invention may take the form of a powdered or particulate substance, which includes the multiple types of transfer factor (not shown). In order to ensure that an appropriate and precise dosage of composition 10 is administered to a subject (not shown), composition 10 may be contained within a gelatin capsule 12 of a type which is well-known and readily available to those in the art. The result is the illustrated capsule 14. Alternatively, a composition according to the present invention may be embodied as tablet, a so-called "caplet," an unencapsulated powder, a liquid, a gel, or in any other pharmaceutically acceptable form. Suitable processes for placing the inventive composition into any such form are readily apparent to those of skill in the art.

In an exemplary embodiment of a method for making or forming a composition according to the present invention, a first type of transfer factor may be combined with a second type of transfer factor. Additionally, one or more other types of transfer factor may be combined with the first and second types of transfer factor. The different types of transfer factor that are combined may be substantially purified transfer factor, components or "products" that include transfer factor, or any combination thereof.

Figure 2:
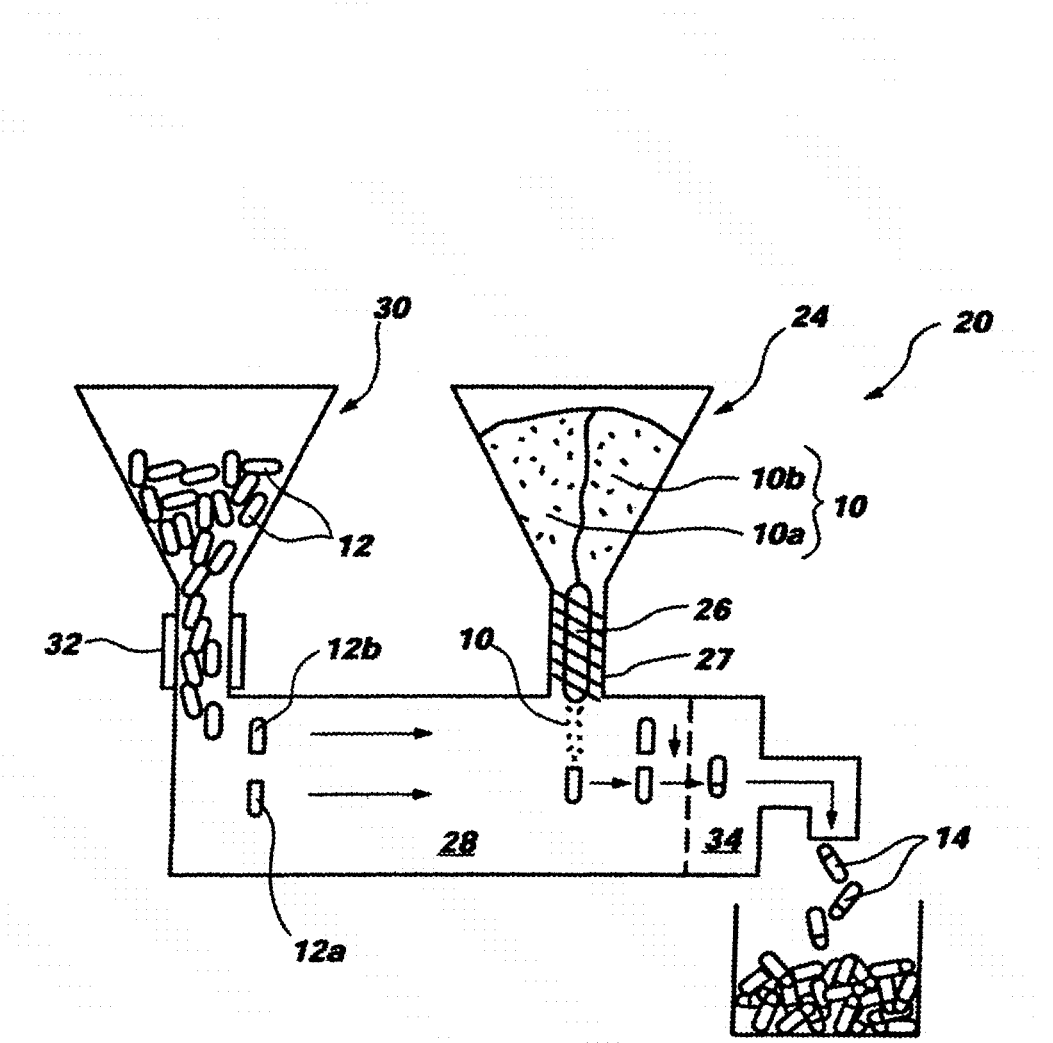
FIG. 2 is a schematic representation of capsulation equipment that may be used to introduce a powdered embodiment of the composition of the present invention into gelatin capsules.

Turning again to FIG. 2, a process for forming composition-filled capsules 14, such as that shown in FIG. 1, is provided merely as an example for a method for making a composition that incorporates teachings of the present invention. As illustrated, the composition 10 is made and composition-filled capsules 14 are formed using standard capsulation equipment 20 of a type known in the industry, such as the SF-135 capsule filling machine available from CapPlus Technologies of Phoenix, Ariz.

In addition to one or more composition supply hoppers 24, an auger 26 associated with each composition supply hopper 24, and a feed station 28 with which each auger 26 and the conduit 27 within which auger 26 is contained communicates, capsulation equipment 20 includes one or more capsule hoppers 30, as well as a pneumatic feed system 32 for transporting capsule bodies 12a and/or caps 12b to feed station 28.

As the capsulation equipment will introduce the mixture into capsules, which may be swallowed by a subject, it is currently preferred that the substantially fat-free component and the egg-derived product be introduced into the capsulation equipment in powdered form. The substantially fat-free component dilutes the amount, or concentration, of fat (e.g., from egg yolk) present in the mixture relative to the concentration of fat which is present in the egg-derived product. Accordingly, the relative amounts of substantially-fat free product and the egg-derived product may be tailored to provide a fat concentration that will minimize clogging of the capsulation equipment.

Continuing with the example of a composition 10 which includes a colostrum-derived product 10a as the substantially fat-free component and an egg-derived product 10b, colostrum-derived product 10a and egg-derived product 10b may be introduced simultaneously into a single composition supply hopper 24 of capsulation equipment 20. For example, colostrum-derived product 10a and egg-derived product 10b may be mixed upon introduction thereof into composition supply hopper 24, as shown, or premixed. By introducing a substance which has a lower fat content than egg-derived product 10b into composition supply hopper 24 along with egg-derived product 10b, the fat content (e.g., concentration) of the resulting mixture is less than that of egg-derived product 10b, reducing or eliminating the likelihood that composition supply hopper 24, auger 26, conduit 27, feed station 28, or any other component of capsulation equipment 20 will be coated with cholesterol or fat.

Following introduction of a predetermined amount of composition 10 into capsule bodies 12a at feed station 28, the filled capsule bodies 12a are transported to a capsule closing station 34, where capsule caps 12b are assembled therewith to fully contain composition 10 within capsule 12.

Again, a composition-filled capsule 14 is only one example of the manner in which a composition that incorporates teachings of the present invention may be embodied. The inventive composition may also take other forms, such as tablets, caplets, loose powder, liquid, gel, liquid-filled or gel-filled capsules, any other pharmaceutically acceptable form known in the art, each of which may be made by known processes.

The composition of the present invention may be administered to a subject (e.g., a mammal, such as a human, a dog, or a cat, a bird, a reptile, a fish, etc.) by any suitable process (e.g., enterally, parenterally, etc.), depending, of course, upon the form thereof. For example, virtually any form of the composition (e.g., a capsule, tablet, caplet, powder, liquid, gel, etc.) may be administered orally (i.e., through the mouth of the subject), provided that the composition includes a pharmaceutically acceptable carrier of a type known in the art that will prevent degradation or destruction of transfer factor molecules by the conditions that persist in the digestive tract of the subject without substantially interfering with the efficacy of the transfer factor molecules included in the composition.

The dosage of composition or transfer factor within the composition that is administered to the subject may depend on a variety of factors, including, without limitation, the subject's weight, the health of the subject, or conditions (e.g., pathogens) to which the subject has been exposed.

Administration of the composition to the subject may cause the immune system of the subject to elicit a T-cell mediated immune response against one or more antigens or pathogens. Thus, the composition may be administered to a subject to treat a disease state that the subject is experiencing, to prevent the subject from exhibiting a disease state caused by a particular pathogen, or to merely enhance the overall health of the subject's immune system and abilities to fight off infecting or invading pathogens.

The following EXAMPLES illustrate the enhanced ability of a composition which includes transfer factors from multiple types of source animals to cause an immune system of a treated subject to elicit a T-cell mediated immune response to various types of pathogens, in the form of target cells. The ratios used in the EXAMPLES are based on the weight of the material (e.g., egg powder, colostrum powder) used in a particular test sample.

Example 1

In EXAMPLE 1, a preliminary test, the target cells included bacteria (e.g., *C. pneumoniae* and *H. pylori*) and viruses (e.g., herpes simplex virus-1 (HSV-1) and herpes simplex virus-2 (HSV-2)) in the form of virally infected cells, as well as to cancerous, or malignant, cells (e.g., K562 erythroleukemic cells).

The in vitro technique that was used to make these determinations was the so-called "chromium-51 release assay," which includes measurement of the amount of radioactive chromium-51 (Cr-51) released by cells that have been attacked by NK cells. The radioactivity measurement may be obtained, for example, with a Beckman 2000 Gamma Counter, which is available from Beckman Coulter, Inc., of Fullerton, Calif.

In EXAMPLE 1, which was a preliminary test, a fixed amount (5 micrograms per milliliter of nutrient media and cellular milieu) of a powdered composition was provided in the nutrient media and cellular milieu, along with a substantially fixed amount of NK cells. Examples of the powdered compositions that were used include bleached wheat flour, Transfer Factor™ (TF), available from 4Life Research, LLC, of Sandy, Utah, Transfer Factor Plus' (TFP or TF+), also available from 4Life Research, avian transfer factor available in a lyophilized (i.e., freeze-dried) whole egg powder, and mixtures of TF and TFP (both the formula marketed in the United States and that marketed internationally) with avian transfer factor in a ratio of about 85% TF or TFP (i.e., bovine transfer factor), by weight, to about 15% avian transfer factor, by weight. The powdered composition, nutrient media, NK cells, and target cells were mixed and incubated for four hours prior to measuring the radioactive atoms that were released by disruption of the target cells by the NK cells. Each exemplary reaction was conducted in triplicate, with the results of the three reactions having been averaged.

In addition to including one or more types of transfer factor, TFP includes a variety of other components, including maitake and shiitake mushrooms, cordyceps, inositol hexaphosphate, beta glucans, beta sitosterol, and olive leaf extract. Maitake and shiitake mushrooms are known to be good sources for polysaccharides and to promote T-cell function. Cordyceps are also rich in polysaccharides. Beta glucans, another class of polysaccharides, is also known to be an important immune cell stimulator.

The following TABLE includes data of the counts per minute obtained with each combination of target cells and powdered composition, as well as the effectiveness of each powdered composition in eliciting an NK cell-mediated immune response against the target cells relative to the NK cell-mediated immune response relative to (measured in percent increase) the same types and concentrations of target cells in the presence of bleached wheat flour.

Example 1

TABLE 1

| | Target Cells | | | | |
|---|---|---|---|---|---|
| | C. Pneu | H. Pyl | K562 Spontaneous | HSV-1 | HSV-2 |
| Flour | 1,256/ | 1,875/ | 1,620/ | 974/ | 1,476/ |
| Average | 1,323/ | 1,121/ | 1,267/ | 2,017/ | 1,262/ |
| Composition | 1,290/ | 1,498/ | 1,444/ | 1,496/ | 1,365/ |
| TF | 2,593/ | 2,499/ | 2,445/ | 2,240/ | 2,473/ |
| % increase over flour | 96% | 123% | 93% | 11% | 96% |
| % increase over average | 101% | 67% | 69% | 50% | 81% |
| TFP | 3,386/ | 2,701/ | 3,243/ | 2,944/ | 1,956/ |
| % increase over flour | 156% | 141% | 156% | 46% | 55% |
| % increase over average | 163% | 80% | 125% | 97% | 43% |
| Bov-Av TF | 14,857/ | 11,434/ | 6,639/ | 17,910/ | 10,626/ |
| % increase over flour | 1023% | 920% | 424% | 788% | 742% |
| % increase over average | 1052% | 663% | 360% | 1098% | 679% |
| Bov-Av TFP US | 6,196/ | 5,543/ | 4,008/ | 8,050/ | 4,693/ |
| % increase over flour | 458% | 485% | 306% | 389% | 362% |
| % increase over average | 380% | 270% | 178% | 438% | 244% |
| Bov-Av TFP Intl | 5,747/ | 4,786/ | 3,640/ | 7,366/ | 4,269/ |
| % increase over flour | 424% | 417% | 277% | 355% | 328% |
| % increase over average | 346% | 219% | 152% | 393% | 213% |
| 100% Avian TF | 2,553/ | 1,860/ | 2,483/ | 2,985/ | 2,183/ |
| % increase over flour | 93% | 66% | 96% | 48% | 73% |
| % increase over average | 98% | 24% | 72% | 100% | 60% |

Notably, the formulations denoted "TFP" include only about half (0.466667) of the transfer factor as that present in the formulations denoted "TF." Accordingly, one of ordinary skill in the art would expect the data that corresponds to cytotoxicity induced by the products identified as "Bov-Av TFP US" and "Bov-Av TFP Intl" to be somewhat less than the cytotoxicity induced by the product identified as Bov-Av TF. Instead, these numbers were much higher. In fact, it appears that the data that corresponds to "Bov-Av TFP US" and "Bov-Av TFP Intl" is about ten times too high. Accordingly, appropriate corrections have been made to TABLE 1. Additionally, further testing has been conducted, as is evident from the ensuing EXAMPLES, to evaluate and verify the abilities of combinations of different types of transfer factor to elicit T-cell responses in treated animals.

The preliminary results that are set forth in TABLE 1 show that administration of a composition of the present invention to a subject will likely increase the subject's secondary, or delayed-type hypersensitivity, immune response, as effected by NK cells, against one or more pathogens to a degree which far exceeds the NK cell activity initiated by both colostrum-derived transfer factor and egg-derived transfer factor alone. In fact, the results show that a composition that incorporates teachings of the present invention may result in facilitation of the activity of NK cells with an unexpected degree of synergy.

In view of these results, further experimentation was conducted to determine the efficacy of a broader range of aspects of the present invention.

Example 2

Figure 3:
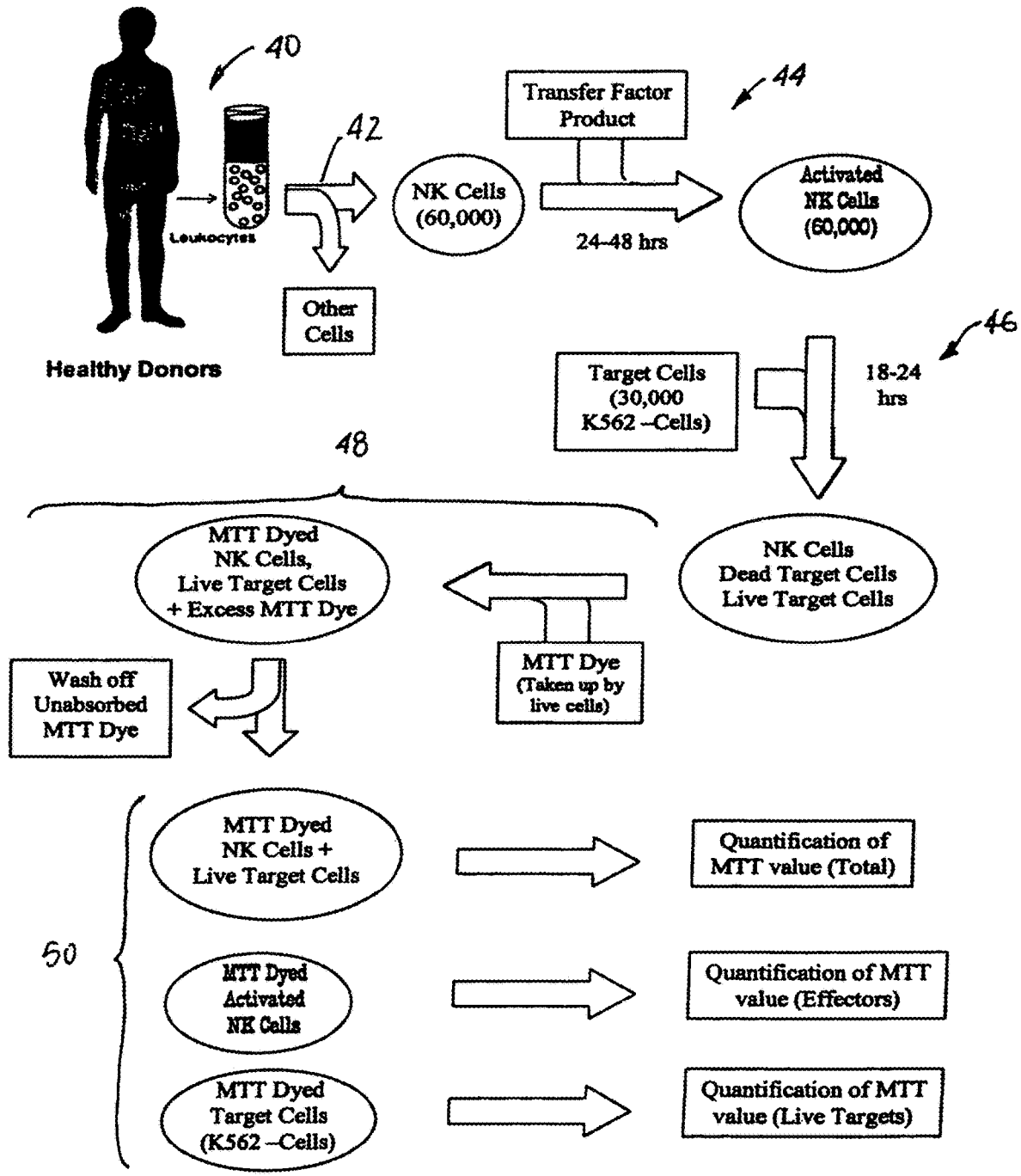
FIG. 3 schematically illustrates an exemplary test protocol that was conducted to determine the efficacy of various aspects of the present invention.

The effects of various transfer factor compositions, including compositions that incorporate teachings of the present invention, on the activity of lymphocytes in attacking cancer cells was evaluated. FIG. 3 schematically represents the protocol for the evaluation. Blood from healthy donors was obtained, at reference 40. Mononuclear cells, including natural killer cells, were separated from other constituents of the blood, at reference character 42, by standard phycol-urographin methodology, employing a density gradient p=i, 077 g/cm$^3$. The isolated mononuclear cells, or "effector cells," at a dilution of about 60,000 cells/100 μl of culture medium, were then introduced in 100 μl aliquots into the wells of a 96-well microtitre plate, such as that available from Corning Incorporated of Corning, N.Y., under the trade name COSTAR®, as shown at reference character 44.

Thereafter, transfer factor-containing test samples, or "additives," as noted in TABLES 2 through 5 below, were introduced into each well, with resulting concentrations of transfer factor in the test samples being 1 mg/ml, 0.1 mg/ml, 0.01 mg/ml, 0.001 mg/ml, 0.0001 mg/ml, and 0.00001 mg/ml, as is also shown at reference character 44. A control including no transfer factor product was also employed. The microtitre plates were then placed in a CO$_2$-incubator with conditions of 5% CO$_2$ atmosphere, 100% humidity, and a temperature of 37° C., and incubated for periods of 24 hours and 48 hours. Each study variant was conducted in triplicate.

After incubation, about 30,000 K-562 tumor cells (i.e., erythroblastotic human leukemia), or "target cells," were introduced into each well, as illustrated at reference character 46, providing a ratio of effector cells-to-target cells of about 2:1. The effector and target cells were then incubated for periods of 18 hours and 24 hours in the CO$_2$ incubator, under the same conditions listed above.

Thereafter, at reference character 48, the MTT method of defining the viability of cellular cultures, which employs a soluble yellow bromide, 3-(4,5-dimethylthiasol-2-il)-2,5-tetrazol (MTT), was used to determine the number of K-562 tumor cells that were killed in each well. In such a test, live cells reduce the MTT to insoluble purple-blue intracellular crystals of MTT-formazan (MTT-f). Nonviable dead cells are not capable of reducing the MTT to MTT-f. Thus, the optical properties of the resulting solution may be evaluated to provide an indication of the affect of various transfer factor-containing products on the ability of the effector cells to kill the K-562 tumor cells. More specifically, the intensity of MTT transformation into MTT-f reflects the general level of the studied cells' dehydrogenase activity and is modulated by the activity of conjugated fermentation systems; e.g., respiratory chain of electrons transmission, etc.

The MTT solution used in this EXAMPLE was prepared in 5 mg/ml of Henks' saline solution, as known in the art. Equal volume aliquots of the MTT solution were introduced into the wells of the microtitre plates, and the plates were incubated in a $CO_2$ incubator, under the same conditions noted above, for a period of about three to about four hours. The microtitre plates were then centrifuged at about 1,500 rpm for about 5 minutes, the supernatant was removed, and 150 μl aliquots of dimethylsulfoxide (DMSO) were introduced into the wells.

The microtitre plates were then permitted to sit at room temperature for a period of thirty minutes, allowing formazan crystals to completely dissolve. Thereafter, a multiwell spectrophotometer (LABSYSTEMS MultiScan MSS 340, available from Cambridge Scientific Products of Cambridge, Mass.) was used to evaluate each well of each microtitre plate at a wavelength of 540 nm.

As shown at reference character 50, the optical density (OD) measurements that were obtained with the spectrophotometer were then used to calculate the cytotoxic index (%) (CI (%)) of each well. The CI (%) calculation was performed according to the standard formula:

$$CI(\%) = [I - (OD_{e+t} - OD_e)/OD_t] * 100,$$

where ODe+t is the OD in experimental series, ODe is the OD in wells including only effector cells, and $OD_t$ is the OD in the wells including only target cells.

TABLE 2

| | CI (%) at 24 Hours | | | | | |
|---|---|---|---|---|---|---|
| Additive | 1 mg/ml | $10^{-1}$ mg/ml | $10^{-2}$ mg/ml | $10^{-3}$ mg/ml | $10^{-4}$ mg/ml | $10^{-5}$ mg/ml |
| TF (bovine) | 35 | 17 | 29 | 18 | 18 | 15 |
| TF+ (international formulation) | 13.5 | 20.3 | 35 | 28.5 | 10 | 20.3 |
| TF+ (85:15, bovine:avian) | 13.3 | 10.6 | 29 | 30 | 21.6 | 76 |
| TF (70:30, bovine:avian) | 80 | 47 | 24 | 12 | 30 | 26.3 |
| TF (avian) | 16 | 37 | 47 | 47 | 16.1 | 34.3 |
| None (spontaneous cell death) (±6%) | 18 | 18 | 18 | 18 | 18 | 18 |

TABLE 3

| | % Increase in CI (over spontaneous CI) at 24 Hours | | | | | |
|---|---|---|---|---|---|---|
| Additive | 1 mg/ml | $10^{-1}$ mg/ml | $10^{-2}$ mg/ml | $10^{-3}$ mg/ml | $10^{-4}$ mg/ml | $10^{-5}$ mg/ml |
| TF (bovine) | 94 | -6 | 61 | 0 | 0 | -17 |
| TF+ (international formulation) | -25 | 13 | 94 | 58 | -44 | 13 |
| TF+ (85:15, bovine:avian) | -26 | -41 | 61 | 67 | 20 | 322 |
| TF (70:30, bovine:avian) | 344 | 161 | 33 | -33 | 67 | 46 |
| TF (avian) | -11 | 106 | 161 | 161 | -11 | 91 |
| None (spontaneous cell death) (±6%) | 0 | 0 | 0 | 0 | 0 | 0 |

TABLE 4

| | CI (%) at 48 Hours | | | | | |
|---|---|---|---|---|---|---|
| Additive | 1 mg/ml | $10^{-1}$ mg/ml | $10^{-2}$ mg/ml | $10^{-3}$ mg/ml | $10^{-4}$ mg/ml | $10^{-5}$ mg/ml |
| TF (bovine) | 19.3 | 50 | 54.7 | 15.3 | 40.7 | 11.3 |
| TF+ (international formulation) | 23.3 | 12 | 17 | 42 | 48 | 62 |
| TF+ (85:15) | 48 | 82.7 | 96.7 | 69.4 | 54 | 91 |
| TF (70:30) | 97 | 94 | 99 | 90 | 96 | 91 |
| TF (avian) | 68 | 49 | 45 | 35 | 58 | 70 |
| None (spontaneous cell death) (±6%) | 18 | 18 | 18 | 18 | 18 | 18 |

TABLE 5

| | % Increase in CI (over spontaneous CI) at 48 Hours | | | | | |
|---|---|---|---|---|---|---|
| Additive | 1 mg/ml | $10^{-1}$ mg/ml | $10^{-2}$ mg/ml | $10^{-3}$ mg/ml | $10^{-4}$ mg/ml | $10^{-5}$ mg/ml |
| TF (bovine) | 7 | 178 | 204 | -15 | 126 | -37 |
| TF+ (international formulation) | 29 | -33 | -6 | 133 | 167 | 244 |
| TF+ (85:15, bovine:avian) | 167 | 359 | 437 | 286 | 200 | 406 |
| TF (70:30, bovine:avian) | 439 | 422 | 450 | 400 | 433 | 406 |
| TF (avian) | 278 | 172 | 150 | 94 | 222 | 289 |
| None (spontaneous cell death) (±6%) | 0 | 0 | 0 | 0 | 0 | 0 |

The data provided in TABLES 2 through 5 confirms that the majority of test samples (i.e., transfer factor-containing compositions) stimulated increased (relative to spontaneous tumor cell death) antitumor and cytotoxic activity of healthy donors' lymphocytes against K-562 tumor cells.

The greatest stimulating effect appears in the 48 hour results, with the most effective range of stimulating concentrations being from about 0.1 mg/ml to about 0.0001 mg/ml. The test samples that included both colostrum-derived transfer factor and egg-derived transfer factor again appear to be the most effective in the given conditions of the experiment, lysing as many as 80-98% of the K-562 tumor cells.

Additionally, the results of TABLE 5 indicate that combinations of different types of transfer factor, particularly the 85:15 ratio of TF+ to egg-derived transfer factor, may be more effective than other courses of therapy for eliminating undesirable cells and pathogens from the body of a treated animal. More specifically, inasmuch as the inventors are aware, in equivalent testing, the best results that could be achieved with interleukin-2 treatment have been 76% cytotoxicity of K-562 tumor cells with a 24 hour incubation (which amounts to a 322% increase over spontaneous deaths of such cells) and an 88% cytotoxicity of K-562 tumor cells with a 48 hour incubation (which amounts to a 389% increase over spontaneous deaths of such cells).

Example 3

Another confirmatory test was conducted to verify the above-stated results and to evaluate the effects of a greater variety of compositions of the present invention on inducing NK and other mononuclear cells to kill K-562 tumor cells. The same protocol described in EXAMPLE 2 was employed in the tests of EXAMPLE 3.

The results of 24 and 48 hour incubation periods for a variety of compositions formulations, each including egg powder and bovine colostrum powder, are listed in TABLES 6 through 9.

TABLE 6

CI (%) at 24 Hours

| Bovine:Avian | 1 mg/ml | $10^{-1}$ mg/ml | $10^{-2}$ mg/ml | $10^{-3}$ mg/ml | $10^{-4}$ mg/ml |
|---|---|---|---|---|---|
| 85:15 | 45 | 29 | 67.5 | 28 | 50 |
| 50:50 | 67.5 | 23 | 66 | 63.5 | 22.5 |
| 30:70 | 64.6 | 68.8 | 39.1 | 45.6 | 44 |
| 15:85 | 55.2 | 28 | 20.1 | 20 | 18.8 |
| None (spontaneous cell death) (±6%) | 18 | 18 | 18 | 18 | 18 |

TABLE 7

% Increase in CI (over spontaneous CI) at 24 Hours

| Bovine:Avian | 1 mg/ml | $10^{-1}$ mg/ml | $10^{-2}$ mg/ml | $10^{-3}$ mg/ml | $10^{-4}$ mg/ml |
|---|---|---|---|---|---|
| 85:15 | 150 | 61 | 275 | 56 | 178 |
| 50:50 | 275 | 28 | 267 | 253 | 25 |
| 30:70 | 259 | 282 | 117 | 153 | 144 |
| 15:85 | 207 | 56 | 12 | 11 | 4 |
| None (spontaneous cell death) (±6%) | 0 | 0 | 0 | 0 | 0 |

TABLE 8

CI (%) at 48 Hours

| Bovine:Avian | 1 mg/ml | $10^{-1}$ mg/ml | $10^{-2}$ mg/ml | $10^{-3}$ mg/ml | $10^{-4}$ mg/ml |
|---|---|---|---|---|---|
| 85:15 | 46 | 60 | 69 | 67 | 64 |
| 50:50 | 69 | 74 | 74 | 63 | 49 |
| 30:70 | 75 | 83 | 67 | 63 | 45 |
| 15:85 | 77 | 69 | 51 | 42 | 40 |
| None (spontaneous cell death) (±6%) | 18 | 18 | 18 | 18 | 18 |

TABLE 9

% Increase in CI (over spontaneous CI) at 48 Hours

| Bovine:Avian | 1 mg/ml | $10^{-1}$ mg/ml | $10^{-2}$ mg/ml | $10^{-3}$ mg/ml | $10^{-4}$ mg/ml |
|---|---|---|---|---|---|
| 85:15 | 156 | 233 | 283 | 272 | 256 |
| 50:50 | 283 | 311 | 311 | 250 | 172 |
| 30:70 | 317 | 361 | 272 | 250 | 150 |
| 15:85 | 328 | 283 | 183 | 133 | 122 |
| None (spontaneous cell death) (±6%) | 0 | 0 | 0 | 0 | 0 |

For the sake of comparison, a whole colostrum sample and a processed transfer factor sample including 100% bovine transfer factor sample (and no avian transfer factor), each including 0.01 mg/ml of transfer factor, were evaluated. At 24 hours, the whole colostrum sample demonstrated a 22% increase in lysis over spontaneous lysis, while the 100% bovine transfer factor sample was responsible for a 103% increase in lysis over spontaneous cell lysis. At 48 hours, the increases in cell lysis were 26% and 203%, respectively.

The data of TABLES 6 through 9, particularly of TABLES 6 and 8, shows that when more colostrum-derived transfer factor is present in a composition according to the present invention (e.g., 85:15), the initial (24 hour test) response may be greater than the response generated by compositions that include less colostrum-derived transfer factor, but does not increase significantly over time (48 hour test).

Compositions (e.g., 50:50 and 30:70) that include more egg-derived transfer factor may provide comparable short term results (24 hour test), but provide much better long term (48 hour test) results.

These results support the theory that combining different types of transfer factors provides a synergistic effect. They also indicate that the proportions of different types of transfer factor in a composition may be tailored to provide a desired result.

Example 4

TABLE 10

| | | CI (%) | | | | | |
|---|---|---|---|---|---|---|---|
| | | 1 mg/ml | $10^{-1}$ mg/ml | $10^{-2}$ mg/ml | $10^{-3}$ mg/ml | $10^{-4}$ mg/ml | $10^{-5}$ mg/ml |
| 24 hrs. | TF+ (85:15) (colostrum:egg) | 13.3 | 10.6 | 29 | 30 | 21.6 | 76 |
| | 85:15 (colostrum:egg) | 45 | 29 | 67.5 | 28 | 50 | |
| 48 hrs. | TF+ (85:15) (colostrum:egg) | 48 | 82.7 | 96.7 | 69.4 | 54 | 91 |
| | 85:15 (colostrum:egg) | 46 | 60 | 69 | 67 | 64 | |

EXAMPLE 4 compares data obtained in EXAMPLES 2 and 3 above to illustrate that the inclusion of additional components, primarily polysaccharides, in TFP improves the efficiency with which a composition that incorporates teachings of the present invention induces NK and other mononuclear blood cells to kill K-562 tumor cells and, thus, elicits a secondary immune response.

Notably, in the 48 hour test, where polysaccharides were included, cytotoxicity was greater at all dilutions above 0.0001 mg/ml than in comparable compositions that lacked polysaccharides. Thus, polysaccharides are believed to either increase the synergism with which the two or more types of transfer factors act or to provide additional synergism in the elicitation of a secondary immune response.

While the foregoing EXAMPLES and accompanying data demonstrate the effectiveness of compositions that include transfer factor and, in particular, compositions that include two or more different types of transfer factor, in eliciting a T-cell (e.g., NK cell) mediated immune response, transfer factor is also believed to affect the immune system of a treated subject in a number of other ways. For example, and not to limit the scope of the present invention, transfer factor may provide the biochemical benefits disclosed in U.S. patent application Ser. No. 11/122,430, filed May 4, 2005, the disclosure of which is hereby incorporated herein, in its entirety, by this reference. As the benefits of transfer factor are not limited to elicitation of T-cell mediated immune responses, synergy in the biochemical effects of transfer factor may also be recognized when two or more types of transfer factor are combined.

Although the foregoing description contains many specifics, these should not be construed as limiting the scope of the present invention, but merely as providing illustrations of some of the presently preferred embodiments. Similarly, other embodiments may be devised without departing from the spirit or scope of the present invention. Features from different embodiments may be employed in combination. The scope of the invention is, therefore, indicated and limited only by the appended claims and their legal equivalents rather than by the foregoing description. All additions, deletions and modifications to the invention as disclosed herein which fall within the meaning and scope of the claims are to be embraced thereby.

What is claimed:

1. A component consisting of:
   a fraction and/or an extract of bovine colostrum comprising mammalian transfer factor; and
   chicken egg yolk comprising avian transfer factor.

2. The component of claim 1, wherein the fraction and/or extract of bovine colostrum is a fraction of bovine colostrum.

3. The component of claim 2, wherein the fraction of bovine colostrum is substantially free of fat.

4. The component of claim 3, wherein the fraction of bovine colostrum is substantially free of at least one of casein, cells, cell debris, antibodies, and allergenic agents.

5. The component of claim 1, wherein the fraction and/or extract of bovine colostrum is an extract of bovine colostrum.

6. The component of claim 1, wherein the chicken egg yolk is a fraction of chicken egg yolk.

7. The component of claim 1, wherein the chicken egg yolk is an extract of chicken egg yolk.

8. The component of claim 1, wherein the fraction and/or extract of bovine colostrum is dried bovine colostrum and the chicken egg yolk is dried chicken egg yolk.

9. The component of claim 1, wherein the fraction and/or extract of bovine colostrum and the chicken egg yolk of the component are selected, and amounts and relative proportions of the fraction and/or extract of bovine colostrum and the chicken egg yolk in the component are tailored, to synergistically elicit an elevated cell-mediated immune response in a treated subject.

10. The component of claim 9, wherein the relative proportions of the fraction and/or extract of bovine colostrum and the chicken egg yolk in the component are further tailored to maintain the elevated cell-mediated immune response for a period of at least 48 hours.

11. A component consisting of:
    a fraction and/or an extract of bovine colostrum including mammalian transfer factor; and
    a fraction and/or extract of chicken egg yolk including avian transfer factor.

12. The component of claim 11, wherein the fraction and/or extract of bovine colostrum and the fraction and/or extract of chicken egg yolk are in dry form.

13. The component of claim 11, wherein amounts and relative proportions of the fraction and/or extract of bovine colostrum and the fraction and/or extract of chicken egg yolk are tailored to synergistically elicit an elevated cell-mediated immune response in a treated subject.

14. The component of claim 13, wherein the relative proportions of the fraction and/or extract of bovine colostrum and the fraction and/or extract of chicken egg yolk are further tailored to maintain the elevated cell-mediated immune response for a period of at least 48 hours.

15. A component consisting of:
    a fraction and/or extract of a source of mammalian transfer factor, said fraction and/or extract comprising mammalian transfer factor; and
    an avian transfer factor-containing component.

16. The component of claim 15, wherein the fraction and/or extract of the source of mammalian transfer factor and the avian transfer factor-containing component are in dry form.

17. The component of claim 15, wherein amounts and relative proportions of the fraction and/or extract of the source of mammalian transfer factor and the avian transfer factor-containing component are selected to synergistically elicit an elevated cell-mediated immune response in a treated subject.

18. The component of claim 17, wherein the relative proportions of the fraction and/or extract of the source of mammalian transfer factor and the avian transfer factor-containing component are further tailored to maintain the elevated cell-mediated immune response for a period of at least 48 hours.

* * * * *